United States Patent [19]
Kranz

[11] Patent Number: 5,152,798
[45] Date of Patent: Oct. 6, 1992

[54] ENDOPROSTHESIS

[75] Inventor: Curt Kranz, Berlin, Fed. Rep. of Germany

[73] Assignee: Johnson & Johnson, New Brunswick, N.J.

[21] Appl. No.: 452,739

[22] Filed: Dec. 21, 1989

[30] Foreign Application Priority Data

Dec. 23, 1988 [DE] Fed. Rep. of Germany ....... 3844157

[51] Int. Cl.⁵ .................................................. A61F 2/32
[52] U.S. Cl. .......................................... 623/22; 623/23
[58] Field of Search ............................... 623/22, 23, 18

[56] References Cited

U.S. PATENT DOCUMENTS

| | | | |
|---|---|---|---|
| 3,314,420 | 4/1967 | Smith et al. | 623/23 |
| 4,287,617 | 9/1981 | Tornier. | |
| 4,595,393 | 6/1986 | Anapliotis et al. | 623/22 |
| 4,718,914 | 1/1988 | Frey et al. | 623/23 |
| 4,792,339 | 12/1988 | Tepi | 623/18 |
| 4,865,608 | 9/1989 | Brooker, Jr. | 623/23 |
| 4,904,262 | 2/1990 | Bensmann | 623/18 |
| 4,904,264 | 1/1990 | Scheunemann | 623/23 |
| 4,919,678 | 4/1990 | Kranz | 623/23 |

FOREIGN PATENT DOCUMENTS 243585 11/1987 European Pat. Off. .............. 623/23

OTHER PUBLICATIONS

Smith, T. S., "Characterization of Porous Coatings," *Advances in Biomaterials*, 1987 pp. 34–36.

*Primary Examiner*—Randy C. Shay
*Attorney, Agent, or Firm*—Spencer, Frank & Schneider

[57] ABSTRACT

Endoprosthesis, in particular a hip joint prosthesis, provided with a hollow shaft being implantable in a hollow space of a bone, being of a tubular and curved shape and diminishing with respect to its diameter and material cross-cut, whereby, from the end that is near to the joint towards the end that is far away from the joint, the bending rigidity of the shaft diminishes to a relatively larger extent than the longitudinal rigidity of the shaft.

14 Claims, 1 Drawing Sheet

ENDOPROSTHESIS

CROSS REFERENCE TO RELATED APPLICATION

This application claims the priority of the Federal Republic of Germany application No. P 38 44 157.8 filed Dec. 23rd, 1988, which is incorporated herein by reference.

BACKGROUND OF THE INVENTION

The present invention relates to an endoprosthesis, in particular a hip joint prosthesis, provided with a hollow shaft being implantable in a hollow space of a bone, being of a tubular and curved shape and diminishing with respect to its diameter and material cross-section.

Prosthesis shafts are fixed into the pre-rasped hollow space of a bone during implantation by cementing or, for cement-free implantation, they are conical or wedge-shaped in the direction away from the joint, and are driven into the hollow space so that they are fixed to the bone by pressural friction.

Such a prosthesis is described in DE - A 29 33 237. The local elasticity and rigidity of the prosthesis has been adapted to conform with that of the surrounding bone. The adaptation only occurs in the form of the material cross-sectional widths and their relation to the forces acting in the longitudinal axis of the prosthesis. The cross-section and the wall thickness diminish continuously from the top to the bottom of the shaft. A drawback of this arrangement is that the deformations which occur due to forces not acting in the longitudinal axis do not react in the same way as the deformations in the surrounding bone area. Micromovements and a possible loosening of the prosthesis are the results.

Another prosthesis shaft with an essentially rectangular cross-section is described in EP-A-0 243 585. Openings are provided in the two areas on the longer sides of the cross-section (dorsal and ventral) to reduce the shear forces which occur in the contact area between the prosthesis and the bone when they are strained and deflect. A weighty drawback of this arrangement is that there is a relatively high areal pressure between the shaft and the bone on the two shorter sides of the cross-section (medial and lateral). Additionally, as there is no physiological adaptation of the rectangular cross-section to that of the natural marrow zone, there are stress peaks in the region of the Adams bend. The differing right- and left-sided geometries of the femoral marrow zone have also not been taken into consideration. Although the flex bility of the prosthesis has been increased due to the openings provided in a plane parallel to the main bending plane—as already practiced in the previously discussed prior art DE-A- 29 33 237—this still is not comparable with that of the surrounding bone area.

SUMMARY OF THE INVENTION

It is an object of the invention to provide a prosthesis of the above-mentioned type, in which the deformability of the shaft has been adapted to coincide better with that of the cortical bone tube. This is to be achieved by making the local flexibility of the shaft more similar to that of the bone.

The above and other objects are accomplished according to the invention by utilizing the realization that all known endoprostheses, with the exception of isoelastic prostheses, have a much greater bending and longitudinal rigidity than the cortical bone tube and that this leads to an unstressing of the corticalis ( called stress-shielding). The leap or discontinuity in the rigidity at the end of the shaft furthest away from the joint leads to a discontinuity in the distribution of stress. The sudden rise in the longitudinal rigidity leads to increased callus production due to cortical irritation. This callus production is a drawback if the shaft wants to resettle minimally after operation or if the shaft has to be restruck for fixation. In addition, this condition deviates increasingly from the normal physiological condition. With a prosthesis according to the invention a sudden rise in stress at the end of the shaft furthest away from the joint is prevented due to its smaller bending rigidity. Nevertheless, a sufficient bending and longitudinal rigidity is guaranteed in the area close to the joint.

It has been found, that a non-linearly diminishing bending rigidity and an approximately linearly diminishing longitudinal rigidity in the direction away from the joint towards the shaft end leads to a pysiologically advantageous even load distribution in the bone. The bending rigidity decreases quickly at first from the end that is nearest the joint to the end that is furthest away from the joint from where on (approximately the last half of the shaft) it only decreases slowly.

Discontinuities do therefore not occur in the bending and longitudinal rigidities. A preferred embodiment of the invention is a hollow tubular form diminishing with respect to its diameter and its wall-thickness in the direction towards the end far away from the joint, whereby the outer curved lateral semi-tubular part extends out beyond the inset medial semi-tubular part at the end far away from the joint. In the area far away from the joint, which is then only semi-tubular due the removal of an approximately semi-tubular section, the bending rigidity is dependent on the moment of inertia, whereas there is only a slight decrease of the longitudinal rigidity slightly as this is dependent on the cross-sectional area.

Due to the local adaptation of the bending rigidity of the prosthesis shaft to that of the surrounding bone, the longitudinal rigidity of the shaft in the direction away from the joint towards the shaft end is also increasingly able to follow the bending of the tubular bone when loaded. This is the same as a so-called shafting.

In the case of a hip-joint endoprosthesis the bending rigidity is to be maintained at such a level in the proximal region so as to ensure that the Adams bend is not overstressed due to lateral loads. The spongiosa webs, which were able to take the lateral loading by shear distribution, are removed from this area of the marrow zone during implantation. The bending rigidity of the shaft must decrease in the direction away from the joint towards the shaft end. Such a construction can be realised quite simply by a tube with a continuously changing wall-thickness. Openings and recesses in the tube-wall can also augment or in themselves have the same effect. The openings in the tube-wall are preferably not to be formed in the convex outer side of the shaft with the greatest curvature, as the tensional strains are too great in this region. As notch strains, which can occur at bores or other openings, cause the resistance to fatigue of the prosthesis to diminish, openings should preferably only be formed (parallel to the plane of greatest deformations) if a continuously decreasing wall-thickness over the whole shaft length does not adapt the local rigidity sufficiently.

The titanium-aluminum-vanadium wrought alloy (TiA16V4) is a very suitable material for constructing prostheses due to its good biocompatibility, high resistance to fatigue, and good corrosion-resistance. This material cannot be cast-moulded. That means that the material is worked by forging or by the mould and weld method. Two moulded or forged semi-tubular parts can be welded together to form the hollow shaft.

The preferred embodiment of the endoprosthesis is collarless as it is only, with great difficulty, possible to adapt collar and shaft simultaneously to the load distribution during an operation. If the collar only sits on the shaft, i.e. it does not fit into the shaft, signs of resorption can occur at the Adams bend and this can lead to the prosthesis becoming loose.

The neck part of the preferred embodiment of the prosthesis consists of an attachment cone onto which ball joints with varying diameters and with varying cone lengths can be attached.

The openings in the wall of the hollow shaft can lead to bone material growing into the hollow area of the shaft. This bone material makes it more difficult to remove either a prosthesis or even, in some cases, a loose prosthesis. In further preferred embodiments of the invention measures have been taken either to prevent the bone from growing into the prosthesis or to facilitate the removal of the ingrown bone.

The former is solved by filling the hollow area of the prosthesis with polyethylene or a similar material. The low rigidity of polyethylene does not influence the elasticity and rigidity requirements. A further preferred embodiment is that the surface of the prosthesis is coated with apatite in the region of the openings. This, in addition, prevents polyethylene from coming in direct contact with the bone.

A further preferred means to weaken the shaft wall locally can be carried out by inserting recesses into it. These recesses can be inserted on the inner surface of the shaft, if the hollow shaft is constructed using a number of parts and if the inner concave curved surface is accessible prior to assembly. Otherwise, the recesses can be inserted on the convex curved surface. These must be filled with a suitable material such as Porocoat to facilitate the breaking away of grown-in bone material during explantation.

A further variation, with which an explantation is made possible in the presence of openings, is to attach the prosthesis neck to the prosthesis in such a way that the surgeon is able to remove the prosthesis neck separately and prior to the prosthesis. The surgeon can then remove any of the bone material that may have grown in, out of the opened hollow area of the shaft using a burr or a drilling machine, without damaging the cortical.

DESCRIPTION OF THE PREFERRED EMBODIMENT

Figure 1:
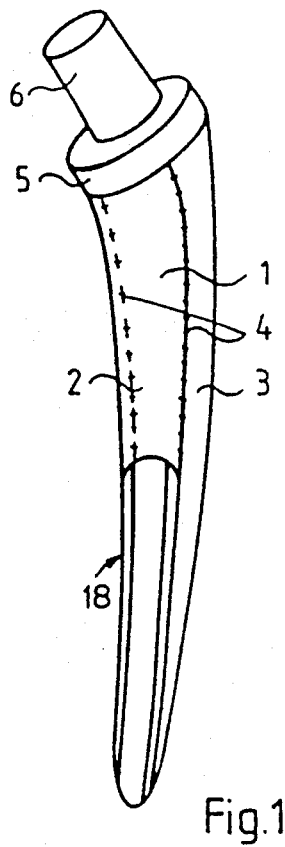
FIG. 1 is a preferred embodiment of an endoprosthesis according to the invention with a disc and cone.

A hollow shaft 1 in the preferred embodiment of an endoprosthesis in FIG. 1 consists of two pressed or forged semi-tubular parts 2 and 3 that are welded together. One of the semi-tubular parts 2 makes up the inner, medial part and the other semi-tubular part 3 the outer, lateral part of the shaft 1. The later part extends out beyond the inset medial part at the end furthest away from the joint by about half a shaft length, the inner and outer lateral parts jointly defining a hollowed out portion or elongated notch 18. This also simplifies construction of a prosthesis as the welding seam 4 which connects the two semi-tubular parts 2 and 3 does not need to extend over the whole length of the shaft 1. A disc 5 is welded to the shaft 1 at the end nearest to the joint. A cone 6 is connected to the disc 5 onto which ball joints with corresponding internal discs can be attached.

The outer form of the shaft 1 is like that of a curved conical tube and is, as such, adapted to coincide with the shape of the natural marrow zone in the femur. A great number of computer-tomographical measurements were taken to enable the confectioning or rafting of the shaft. It has been proven that it is favorable to take the differing geometries of the left and right marrow zones into account, and to produce left and right prostheses with their well-known characteristic additional formations, as these can carry the torsional load better. The embodiments shown in the figures are symmetric and can be implemented for both left and right sides.

Figure 2:
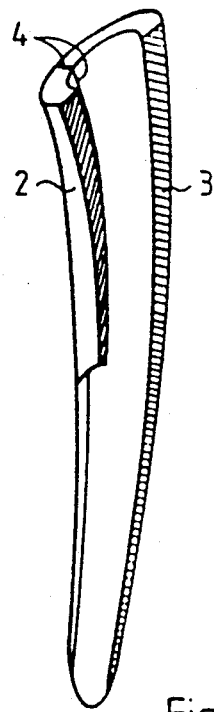
FIG. 2 is a longitudinal section through the hollow shaft of the prosthesis according to FIG. 1.

FIG. 2 illustrates a longitudinal section through the hollow shaft 1 of the prosthesis according to FIG. 1. It can be seen that the wall-thickness of the tubular shaft diminishes in the direction towards the end furthest away from the joint. The constant and continual variation of the wall-thickness means that the longitudinal rigidity of the prosthesis shaft can be adapted well to coincide with that of the bone, whereby stress peaks can be avoided and the area of contact between the shaft and the bone remains uninfluenced.

Figure 3:
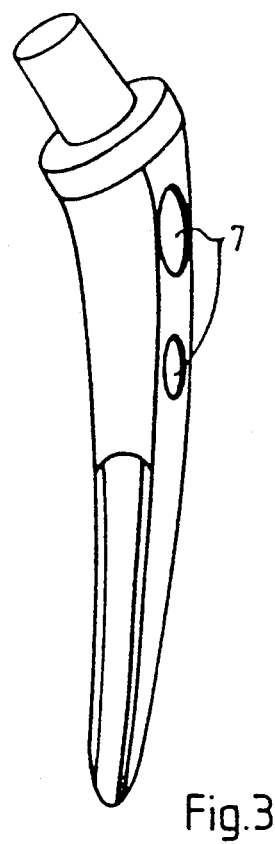
FIG. 3 is a longitudinal section of another preferred embodiment of the endoprosthesis according to the invention with inserted openings.

A further preferred embodiment of the prosthesis according to the invention is illustrated in FIG. 3. The shaft has large openings 7. These openings enhance and augment the effect described hertofore. In general, openings should not be inserted in the convex outer side of the shaft, as this outer part of the shaft is greatly strained.

As notch strains, which can occur at bores or other openings, can be problematic with regard to the durability of the prosthesis, it is suggested that only a small number of larger sized openings are formed. These lower the resistance to bending of the prosthesis in the area of its largest curvature.

Such openings can lead to bone material growing into the hollow area of the shaft, which makes a possible explantation much more difficult. It is therefore better, either to try to prevent the bone from growing into the hollow area of the shaft, or to construct the prosthesis with a joint part which is separable from the shaft. The latter enables the bone to be removed from the inside of the shaft, especially by way of drilling.

Figure 7:
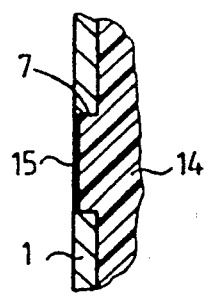
FIG. 7 is a detailed partial section of a further preferred embodiment of the endoprosthesis according to the invention.

The growth of spongiosa into the shaft illustrated in FIG. 3 is prevented by filling the hollow area with polyethylene 14 and covering the polyethylene surface in the openings 7 with a coating 15 of apatite. This variation of the preferred embodiment is enlarged and illustrated in FIG. 7.

Figure 4:
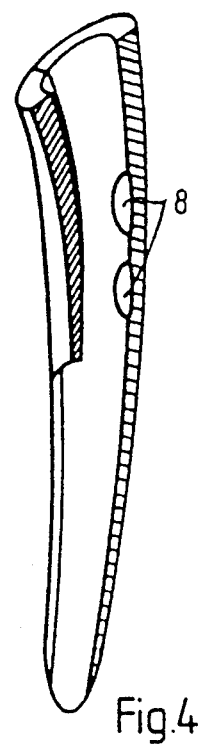
FIG. 4 is a longitudinal section of a further preferred embodiment of the endoprosthesis according to the invention with recesses on the inner surface of the shaft wall.

Another means to weaken the shaft wall locally can be carried out by inserting recesses 8 into the inner side of the shaft wall, as can be seen illustrated in FIG. 4. These recesses 8 can be inserted if the inner surface of the shaft wall is accessible. This is especially the case when the prostheses shafts are produced in a dual-stage production process. In this process the two pressed or forged semi-tubular parts are connected together at a later stage. These semi-tubular parts can, if they have not already been formed during moulding and forging, be additionally worked on with cutting devices, e.g. using chemical milling.

Figure 5:
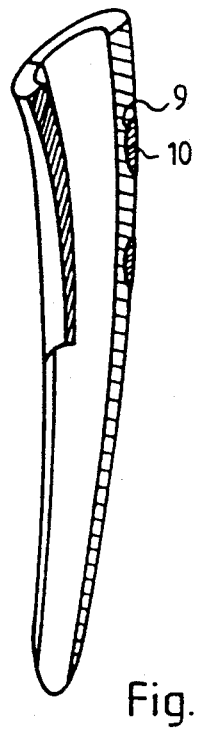
FIG. 5 is a longitudinal section of a further preferred embodiment of the endoprosthesis according to the invention with recesses on the outer surface of the shaft wall.

The insertion of recesses 9 in the outer surface of the prosthesis—see FIG. 5—is also possible. The recesses 9 are filled with a known material 10 such as porocoat to prevent bone material from growing into the recesses. Porocoat is a trademark of De Puy, Inc. an Indiana corporation, and is used in connection with sintered porous metal layer which permits ingrowth of live tissue, sold only as applied to a medical prosthesis.

Figure 8:
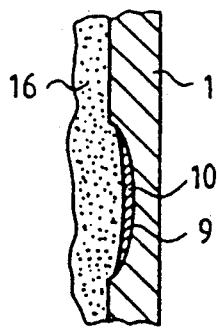
FIG. 8 is a detailed partial section of a further preferred embodiment of the endoprosthesis according to the invention.

In another further embodiment of the invention, as illustrated in FIG. 8, the recesses are not completely filled with Porocoat-coating 10, so that there still exists a small recess in relation to the rest of the prosthesis surface. The bone material 16 which grows into these remaining recesses, together with the Procoat-coating 10 with which it is contact, ensure that the shaft 1 sits tightly. If, however, it is necessary at a later date to remove shaft 1, the in-grown bone material 16 shears away and the prosthesis is free. This is because the cracking plane of the bone material 16 does not form a barrier as it conforms approximately with the surface plane of the adjacent shaft surface. The extremely tight connection between bone 16 and Porocoat material 10 does not have to be severed.

Figure 6:
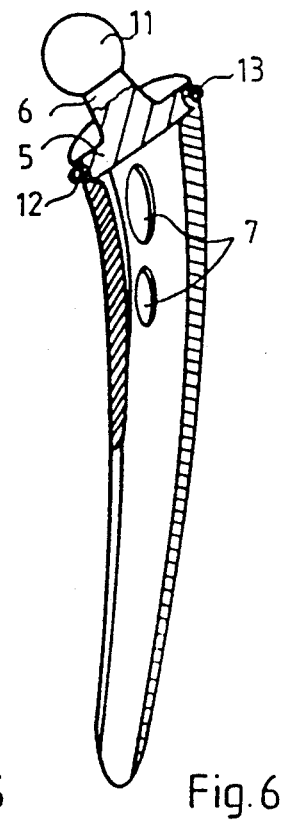
FIG. 6 is a section of a further preferred embodiment of the endoprosthesis according to the invention with a removeable head part.

It is also possible the allow the bone material 16 to grow in through the openings 7 in the prosthesis shaft, in which case it then has to be drilled away from the inside of the prosthesis if an explantation becomes necessary due to a renewed operation. This is only possible, if the hollow area of the shaft 9 is accessible when required. In this case, a disconnectable connection is provided between the hollow shaft 1 and the joint part 11, as illustrated in FIG. 6. The disc 5 of the joint part 11 is connected to the flange-shaped end of the hollow shaft 1 and tightened with an outer bracing ring 12 during implantation. The bracing ring 12 has a predetermined breaking point by way of an area of material weakness 13 so that the joint part 11 can be easily removed, requiring only a small amount of force.

It will be understood that the above description of the present invention is susceptible to various modifications, changes and adaptations, and the same are intended to be comprehended within the meaning and range of equivalents of the appended claims.

What is claimed is:

1. An endoprosthesis comprising:
a hollow shaft being implantable in a hollow space of a bone, said hollow shaft having a joint end and an end distant from said joint end, and being of a tubular and curved shape having an inner curved side and an outer curved side, and said hollow shaft diminishing substantially continuously with respect to its diameter and its cross-sectional area, from the joint end towards the distant end, and the bending rigidity of said shaft and the longitudinal rigidity of said shaft diminishing substantially continuously from said joint end to said end distant from said joint end, wherein the inner curved side of said shaft has an elongated notch extending from said distant end a substantial distance toward and terminating before reaching said joint end to diminish bending rigidity in a corresponding region of said shaft so that the bending rigidity diminishes to a relatively larger extent than the longitudinal rigidity of said shaft.

2. An endoprosthesis as defined in claim 1, wherein a remaining portion of said shaft in the area of said elongated notch is substantially partially tubular.

3. An endoprosthesis as defined in claim 2, wherein said shaft comprises two partially tubular portions, one said partially tubular portion comprises said inner curved side and the other one of said two partially tubular portions comprises said outer curved side, said outer side extending further from said joint end and being longer than said inner curved side.

4. An endoprosthesis as defined in claim 1, wherein said shaft comprises a titanium-aluminum-vanadium alloy.

5. An endoprosthesis as defined in claim 4, wherein said titanium-aluminum-vanadium alloy comprises TiA16V4.

6. An endoprosthesis as defined in claim 1, further comprising means for defining openings in a wall of said hollow shaft.

7. An endoprosthesis as defined in claim 6, wherein said hollow shaft is filled with polyethylene and a surface of the polyethylene is coated wit apatite in a region of said openings.

8. An endoprosthesis as defined in claim 6, further comprising one of a joint and a joint part onto which a joint can be attached detachably connected to the joint end by means of a bracing ring with a predetermined breaking point.

9. An endoprosthesis as defined in claim 8, wherein said joint part comprises an attachment cone.

10. An endoprosthesis as defined in claim 1, further comprising means for defining recesses in one of said inner and outer curved sides of said hollow shaft for weakening the wall.

11. An endoprosthesis as defined in claim 10, wherein said recesses are filled with said material which permits ingrowth of line tissue.

12. An endoprosthesis as defined in claim 11, wherein said recesses are partly filled with said material, and the surface of the recesses partly filled with said material are indented with relation to the rest of the shaft surface.

13. An endoprosthesis as defined in claim 1, wherein at least part of a surface of said endoprosthesis is coated with a material which permits ingrowth of live tissue.

14. An endoprosthesis as defined in claim 1, wherein said hollow shaft is collarless.

* * * * *